United States Patent
Stephan et al.

(10) Patent No.: US 8,067,587 B2
(45) Date of Patent: Nov. 29, 2011

(54) PROCESS FOR THE PRODUCTION OF MONOALKALI METAL CYANURATES

(75) Inventors: Kurt F. Stephan, East Wenatchee, WA (US); Brandon K. Stephan, Wenatchee, WA (US)

(73) Assignee: Lenroc Company, Ephrata, WA (US)

(*) Notice: Subject to any disclaimer, the term of this patent is extended or adjusted under 35 U.S.C. 154(b) by 0 days.

(21) Appl. No.: 11/495,877

(22) Filed: Jul. 28, 2006

(65) Prior Publication Data

US 2007/0032649 A1 Feb. 8, 2007

Related U.S. Application Data

(60) Provisional application No. 60/703,528, filed on Jul. 28, 2005.

(51) Int. Cl.
*C07D 251/32* (2006.01)
*C07D 251/34* (2006.01)

(52) U.S. Cl. .................................. 544/192; 544/190
(58) Field of Classification Search .................. 544/192
See application file for complete search history.

(56) References Cited

U.S. PATENT DOCUMENTS

| 4,233,444 | A | 11/1980 | Doonan et al. |
| 4,432,959 | A | 2/1984 | Shimamura et al. |
| 5,066,408 | A | 11/1991 | Powell |
| 6,207,177 | B1 | 3/2001 | Jany |

*Primary Examiner* — Venkataraman Balasubramanian
(74) *Attorney, Agent, or Firm* — Michael Best & Friedrich LLP

(57) ABSTRACT

A process for making monoalkali metal cyanurates in a powdery form from a cyanuric acid powder by adding thereto a concentrated aqueous solution of an alkali hydroxide such as sodium or potassium hydroxide. The concentrated aqueous alkali hydroxide solution is added sequentially to the cyanuric acid powder as the admixture is vigorously mixed, forming a monoalkali metal cyanurate as a hydrated powder.

20 Claims, No Drawings

PROCESS FOR THE PRODUCTION OF MONOALKALI METAL CYANURATES

PRIORITY CLAIM

The present application claims priority from commonly owned U.S. patent application Ser. No. 60/703,528, filed Jul. 28, 2005, which is incorporated herein by reference.

FIELD OF THE INVENTION

The present invention relates to the production of alkali metal cyanurates and, more particularly, to a process of producing sodium or potassium cyanurate on an industrial scale.

BACKGROUND OF THE INVENTION

Cyanuric acid is a compound that historically has been used as a chlorine stabilizer in swimming pool water. Although widely accepted in the recreational water industry for this use, cyanuric acid has the drawback of being relatively insoluble in water (0.25% at 75° F.) and acidic (pH 2.8 to 4.5). Because acidic chemicals in pool water will cause metal corrosion as well as damage to certain types of pool tile and vinyl liners, the addition of alkaline compounds is required to adjust pool water to an ideal range of pH 7.4 to 7.6.

Monosodium cyanurate has an alkaline pH and is considerably more soluble in water than cyanuric acid and consequently has been of interest to the pool industry. A number of complex approaches exist to produce monosodium cyanurate. Slurry products are described in U.S. Pat. No. 6,207,177 issued to Jany and in U.S. Pat. No. 4,233,444 issued to Doonan et al., wherein alkali metal hydroxides are reacted with cyanuric acid in solution. These methods have the disadvantage of involving considerable quantities of water, generally 60% to 80% by weight, and require expensive filtration and drying equipment as well as sizing machinery to achieve a suitable dry product.

Shimamura et al., in U.S. Pat. No. 4,432,959, disclose a complex method for making sodium cyanurate involving reacting iso cyanuric acid with sodium carbonate or sodium hydrogencarbonate and heating the composition to temperatures between 70 to 100° C.

It would be advantageous and thus there is a need for a less complex procedure to produce an alkali metal cyanurate that does not require heating, uses little water and is produced as a powder.

SUMMARY OF THE INVENTION

Embodiments of the invention for producing a monoalkali metal cyanurate powder comprise adding an aqueous solution of a concentrated monoalkali hydroxide to a cyanuric acid powder, wherein the aqueous solution has a high enough concentration of the monoalkali hydroxide and the aqueous solution is added at a rate slow enough and with sufficient mixing to the cyanuric powder so that a monoalkali metal cyanurate powder is produced. Preferably, the monoalkali hydroxide is either sodium or potassium hydroxide, and is present in solution at a concentration from about 40% to about 60% wt/wt, and preferably 45-55%.

The aqueous solution of the monoalkali hydroxide is preferably sequentially mixed with the cyanuric acid powder over a period of time ranging from about 15 minutes to 24 hours, depending on the amount of the monoalkali cyanurate to be produced. The cyanuric powder should have a moisture content of less than about 20%, and preferably less than 5%, and preferably should have a particle size of less than about 20 mesh.

The process of mixing concentrated aqueous solutions of an alkali hydroxide with a cyanuric powder for the commercial manufacture of an alkali metal cyanurate in powdery form is surprising. One of ordinary skill in the art would reasonably presume that reacting a strong alkaline material like sodium hydroxide or potassium hydroxide with an acidic powder, such as cyanuric acid powder, would release heat rapidly and would form dough-like masses that would jam commercial equipment. To the contrary, the inventors have found that a dry alkali metal cyanurate is produced by the process of the present invention, which process avoids the deficiencies found in the prior art. Thus, processes according to the invention require no additional heating of reactants and yield uniform spherical granules of sodium cyanurate or potassium cyanurate that require no further drying. Only water is released from the heat of reaction.

The products resulting from application of processes according to the invention may be used for a variety of applications. Alkali metal cyanurate dry granules may be combined with other dry pool chemicals to form a composite mix. The materials may also be reconstituted with water to form various suspensions and solutions. They can also be applied directly to pool water or placed in a pool skimmer. The materials are readily suitable as reactants in the formation of chlorinated cyanurates. Because the resultant alkali metal cyanurate is dry, it can be shipped and stored indefinitely.

DETAILED DESCRIPTION OF THE EMBODIMENTS

Definitions

The term "powder" refers to any substance in the form of fine, dustlike particles, produced by crushing or grinding.

The term "alkali metal" refers to a member of the Group 1A metals, which include lithium, sodium, potassium, rubidium, cesium and francium.

The term "monoalkali metal" refers to a compound having only one alkali metal ion per molecule of the compound.

Discussion:

As stated above, the invention relates to a process for producing a monoalkali metal cyanurate powder. The processes generally comprise adding an aqueous solution of a monoalkali hydroxide to a cyanuric acid powder, wherein the aqueous solution has a high enough concentration of the monoalkali hydroxide and the aqueous solution is added at rate slow enough and with sufficient mixing so that a monoalkali metal cyanurate powder is produced. Preferably, the monoalkali hydroxide is either sodium or potassium hydroxide and is present in solution at a concentration of from about 40% to about 60% wt/wt.

In preferred embodiments, the aqueous solution of the alkali metal hydroxide is sequentially mixed with the cyanuric acid powder over a period of time ranging from about 15 minutes to 24 hours, depending on the amount of the monoalkali cyanurate to be produced. The cyanuric powder should have a moisture content of less than about 20%, and preferably less than 5%, and preferably should have a particle size of less than about 20 mesh.

In a preferred embodiment of the invention, a 45% to 55% wt/wt sodium or potassium hydroxide solution is slowly dripped or sprayed into cyanuric acid powder, which is subject to vigorously mixing. The addition of the concentrated aqueous solution of the alkali metal hydroxide is preferably accomplished with minimal clumping. Factors known to affect clumping under the conditions described herein include mixing speed, cyanuric acid particle size, moisture present, and the ratio of reactants during the reaction period.

The cyanuric acid powder should have a moisture content of 20% or less, preferably 5% or less. Excess moisture present in the cyanuric acid powder causes the reactant mixture to form a pasty or dough-like mass wherein the added caustic solution cannot be mixed properly. Additionally, hard lumps of disubstituted or trisubstituted cyanurates can form under these conditions. Moreover, the dough-like material may stick to mixer walls and blades, and likely would require expensive mixing equipment as well as drying and sizing equipment.

During the reaction period between the two admixes, moisture is released as a byproduct. As noted above, increased moisture in the mixture will increase the occurrence of undesirable resulting compositions. Consequently, the lower the moisture content of the cyanuric powder, the faster the caustic solution may be added. For example, the overall reaction time for cyanuric acid with 15% moisture might be 4 hours while the reaction time for cyanuric acid with 5% moisture might be 2 hours.

The particle size of the cyanuric acid powder is also an important variable when attempting to maintain a free flowing, powdery mixture of sodium cyanurates and unreacted cyanuric acid powder. Particle size also directly affects the velocity of the reaction. Generally, the cyanuric acid powder should be below 20 mesh (US. Sieve screen) for optimal results, although higher values will still achieve the benefits of the invention. A representative screen analysis is as follows:

| Mesh Size | % On Screen |
| --- | --- |
| 20 | 0.2 |
| 24 | 0.9 |
| 40 | 22.7 |
| 50 | 40.0 |
| 60 | 22.3 |
| 80 | 3.9 |
| 100 | 3.4 |
| −100 | 6.6 |

When using cyanuric acid powder as sized above, the reactant mixture will remain as a free flowing powder as caustic solution is added. Using cyanuric acid material that is composed of finer particles will speed up the rate of reaction but also causes increased dusting, which may require dust collection equipment.

During the course of the reaction using the parameters described herein, the particle size of the formed sodium or potassium cyanurate will be reasonably equivalent to the particle size of the starting cyanuric acid powder. Mixing equipment, such as a ribbon blender, will form spherical particles during 1 to 6 hours of blending, and yield a free flowing, granular powder, which requires no additional drying or grinding.

The addition of a caustic hydroxide solution, such as a sodium or potassium hydroxide solution, to the cyanuric acid powder causes an exothermic reaction to take place. This beneficial byproduct of reaction further reduces the amount of moisture present in the mix, thereby reducing the presence of undesirable byproducts associated with high moisture content. Moreover, the generation of heat reduces or eliminates the need for external heating of the mixture, depending upon other variables. Without further drying, the resultant alkali metal cyanurate will be a hydrate such as monosodium cyanurate monohydrate. As an anciliary benefit and in contrast to reactions involving the use of sodium carbonate, no $CO_2$ is given off using the process of the present invention.

The reaction of cyanuric acid with sodium hydroxide proceeds on an equimolar basis (based on dry weights) as follows: 1 mole cyanuric acid (129)+1 mole sodium hydroxide (40)=1 mole monosodium cyanurate (151)+1 mole water (18). By adjusting the molar addition of aqueous alkali metal solution, the final content of alkali metal cyanurate may be controlled. For example, if an aqueous solution having a 50% concentration of sodium hydroxide is added to anhydrous cyanuric acid powder, 62 grams of an aqueous solution having a 50% concentration of sodium hydroxide will neutralize 100 g of cyanuric acid to form nearly 100% monosodium cyanurate at a pH of 8.9 on a dry weight basis. Addition of 31 grams of an aqueous solution having a 50% concentration of sodium hydroxide to 100 grams of cyanuric acid powder would form a mixture of 54% monosodium cyanurate and 46% cyanuric acid at a pH of 7.4. The substitution of other alkali metal hydroxides as defined above will yield similar results and are considered well within the scope of the invention as defined in the below claims.

The reaction time of mixing is dependent on the molar addition of the aqueous solution of the alkali metal hydroxide. Generally, the addition of 1 molar equivalent alkali metal hydroxide to cyanuric acid powder will take twice as long as a 0.5 molar addition. The reaction can be terminated any time after the desired aqueous alkali metal hydroxide solution is added, preferably as long as the material has no clumps and is a free flowing powder. Through experimentation and within the ranges of variables expressed herein, the range of the reaction period with mixing is between about 15 minutes to 24 hours, and preferably 1 to 6 hours.

Embodiments of the invention will be understood more readily by reference to the following examples, however, these examples are intended to illustrate the invention and are not to be construed to limit the scope of the invention.

Example 1

25 kg of cyanuric acid powder (supplied by Vopak USA) having a moisture content of 3% was charged into a 5 ft.$^3$ ribbon blender having a 5 horsepower drive (supplied by Aim Blending Technologies). The agitation speed was adjusted to 40 rpm. 6 kg of 50% (wt/wt) sodium hydroxide (supplied by Quadra Chemicals) was slowly dribbled into the mixer through 4 orifices at a rate of 2 kg per hour. Each of the 4 orifices had a diameter of 0.12 inches (0.3048 cm). The reaction temperature reached 43° C. and moisture was released from the mixer. The reaction mixture remained as a free flowing powder during the 3 hour reaction and mixing period. A 1% saturated water solution of the mixture had a pH of 7.5. The molar equivalency of the mixture was 40.4% monosodium cyanurate, 51.9% cyanuric acid, and 7.7% water as determined by drying a 100 g sample at 135° C. for two hours.

Example 2

1000 pounds of cyanuric acid powder having a 2% moisture content was charged to a 35 ft.$^3$ ribbon blender with 15 horsepower drive (supplied by Aim Blending Technologies, serial no. 035-086 HD-15HP0). The agitation speed was adjusted to 45 rpm. 601 pounds of an aqueous solution of 50% (wt/wt) sodium hydroxide was added to the powder through six orifices at the rate of 103 pounds per hour over a six-hour reaction and mixing period. Each of the 6 orifices had a diameter of 0.18 inches (0.4572 cm). The molar equivalency of the mixture was 90.2 monosodium cyanurate, 0.8% cyanuric acid and 9.0% water as determined by drying a 100 g sample at 135° C. for two hours. A 1% saturated water solution had a pH of 9.0.

Example 3

100 grams of cyanuric acid powder having a moisture content of 1% was charged to a stainless steel mixing bowl. 62 grams of an aqueous solution of 45% (wt/wt) potassium hydroxide was sequentially added over one-half hour while mixing with a twin blade (egg-beater type) lab mixer. The reactants initially formed small clumps, which were easily broken up by the blades. As potassium cyanurate formed the powder became free flowing and appeared dry. The reaction yielded 113.5 grams of 92% monopotassium cyanurate. A 1% saturated water solution of the mixture had a pH of 8.1.

What is claimed is:

1. A method for producing a monoalkali metal cyanurate, comprising mixing a monoalkali metal hydroxide with cyanuric acid to form a reaction mixture, wherein the monoalkali metal hydroxide in the reaction mixture reacts with the cyanuric acid in the reaction mixture to form the monoalkali metal cyanurate, and wherein the reaction mixture is a powder.

2. The method of claim 1, wherein the cyanuric acid is a powder, and the mixing step comprises adding the monoalkali metal hydroxide to the cyanuric acid powder.

3. The method of claim 2, wherein the cyanuric acid is comprised of particles of cyanuric acid having a particle size of less than about 20 mesh.

4. The method of claim 2, wherein the cyanuric acid has less than about 20% water by weight.

5. The method of claim 2, wherein the cyanuric acid has less than about 5% water by weight.

6. The method of claim 1, wherein the monoalkali metal hydroxide includes sodium hydroxide or potassium hydroxide.

7. The method of claim 1, wherein water is released from the reaction mixture as a byproduct.

8. The method of claim 1, wherein the monoalkali metal cyanurate forms as a powder without any further processing of the monoalkali metal cyanurate with filtration or drying equipment.

9. A method of making a monoalkali metal cyanurate suspension or solution, comprising reconstituting in water the monoalkali metal cyanurate prepared by the method of claim 1.

10. A monoalkali metal cyanurate suspension or solution prepared by the method of claim 9.

11. A method for producing a monoalkali metal cyanurate, comprising mixing a monoalkali metal hydroxide with cyanuric acid to form a reaction mixture, wherein the monoalkali metal hydroxide in the reaction mixture reacts with the cyanuric acid in the reaction mixture to form the monoalkali metal cyanurate, and wherein the reaction mixture is not a slurry.

12. The method of claim 11, wherein the reaction mixture contains less water than would be required to form a pasty or dough-like mass.

13. The method of claim 11, wherein the reaction mixture is a free flowing powder.

14. The method of claim 11, wherein prior to formation of the reaction mixture the cyanuric acid is a powder having a water content of less than about 20% by weight.

15. The method of claim 11, wherein prior to formation of the reaction mixture the cyanuric acid is a powder having a water content of less than about 5% by weight.

16. The method of claim 11, wherein water is released from the reaction mixture as a byproduct.

17. The method of claim 11, wherein the monoalkali metal cyanurate forms as a powder without any further processing of the monoalkali metal cyanurate with filtration or drying equipment.

18. A method of making a monoalkali metal cyanurate suspension or solution, comprising reconstituting in water the monoalkali metal cyanurate prepared by the method of claim 11.

19. A monoalkali metal cyanurate suspension or solution prepared by the method of claim 18.

20. A method for producing a dry monoalkali metal cyanurate, comprising mixing a monoalkali metal hydroxide with cyanuric acid to form a reaction mixture, wherein the monoalkali metal hydroxide in the reaction mixture reacts with the cyanuric acid in the reaction mixture to form the monoalkali metal cyanurate as a powder.

* * * * *